United States Patent
Momtahan et al.

(10) Patent No.: US 8,213,008 B2
(45) Date of Patent: Jul. 3, 2012

(54) SYSTEMS AND METHODS FOR UTILIZING CYLINDRICAL BEAM VOLUME HOLOGRAMS

(75) Inventors: Omid Momtahan, Foothill Ranch, CA (US); Chao Ray Hsieh, Atlanta, GA (US); Ali Adibi, Suwanee, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 276 days.

(21) Appl. No.: 12/671,166

(22) PCT Filed: Jul. 31, 2007

(86) PCT No.: PCT/US2007/074799
§ 371 (c)(1),
(2), (4) Date: Jan. 28, 2010

(87) PCT Pub. No.: WO2009/017496
PCT Pub. Date: Feb. 5, 2009

(65) Prior Publication Data
US 2010/0201979 A1    Aug. 12, 2010

(51) Int. Cl.
*G01B 9/02* (2006.01)
(52) U.S. Cl. .................... 356/326; 356/451; 356/454
(58) Field of Classification Search ............ 356/326, 356/451–458
See application file for complete search history.

(56) References Cited

U.S. PATENT DOCUMENTS

| | | | | |
|---|---|---|---|---|
| 5,339,305 A | * | 8/1994 | Curtis et al. | 369/103 |
| 5,671,073 A | * | 9/1997 | Psaltis et al. | 359/22 |
| 7,427,932 B2 | * | 9/2008 | Brady et al. | 341/13 |
| 2004/0021871 A1 | * | 2/2004 | Psaltis et al. | 356/451 |
| 2010/0110442 A1 | * | 5/2010 | Adibi et al. | 356/454 |

FOREIGN PATENT DOCUMENTS

JP    2006-154603    *    6/2006

* cited by examiner

Primary Examiner — Layla Lauchman
(74) Attorney, Agent, or Firm — Thomas, Kayden, Horstemeyer & Risley LLP.

(57) ABSTRACT

Systems and methods for performing spectral-spatial mapping in (one and two dimensions) and coded spectroscopy are described. At least one embodiment includes a system for performing spectral-spatial mapping and coded spectroscopy comprising a cylindrical beam volume hologram (CBVH), the CBVH configured to receive input beams and generate diffracted beams in a first direction to perform spectral-spatial mapping, the CBVH further configured to allow input beams to pass in a second direction orthogonal to the first direction unaffected. The system further comprises a first lens configured to receive the diffracted beams and perform a Fourier transform on the input beams in the first direction, a second lens configured to receive the diffracted beams and focus the beams in the second direction to generate output beams, and a charged coupled device (CCD) configured to receive the outputs beams, the output beams used to provide spectral analysis of the input beams.

34 Claims, 10 Drawing Sheets

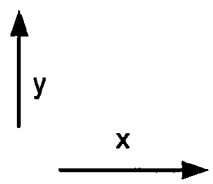
FIG. 5A  FIG. 5B

US 8,213,008 B2

SYSTEMS AND METHODS FOR UTILIZING CYLINDRICAL BEAM VOLUME HOLOGRAMS

STATEMENT REGARDING FEDERALLY SPONSORED RESEARCH OR DEVELOPMENT

This invention was made with Government support under Agreement Number N01AA23013, awarded by the National Institutes of Health. The Government has certain rights in the invention.

CROSS-REFERENCE TO RELATED APPLICATION

This application claims priority to, and the benefit of, PCT Application No. PCT/US2007/074799 entitled, "Systems and Methods for Utilizing Cylindrical beam Volume Holograms," filed on Jul. 31, 2007, which is entirely incorporated herein by reference.

TECHNICAL FIELD

The present disclosure generally relates to the field of spectroscopy and more particularly, relates to utilizing cylindrical beam volume holograms in holographic based slitless spectrometers used to achieve a large spectral operating range and to perform coded spectroscopy.

BACKGROUND

The basic principle behind most spectrometers involves the separation of different wavelength channels within an input beam onto different locations of an output plane using some type of dispersive element. The output may be detected using some type of detector array or a charged coupled device (CCD). Because of the scalar nature of the spectrum, such dispersive elements (e.g., gratings and prisms) generally provide a mapping between the different wavelengths and various spatial locations along a line on the detector. For example, for the case of a simple sinusoidal grating, dispersion is obtained across a line in a direction parallel to the grating vector. Thus, in the direction perpendicular to the grating vector, the light distribution at the output is similar to that at the input and does not carry any additional spectral information.

SUMMARY

Briefly described, one embodiment, among others, includes a system for performing spectral-spatial mapping and coded spectroscopy comprising a cylindrical beam volume hologram (CBVH), the CBVH configured to receive input beams and generate diffracted beams in a first direction to perform spectral-spatial mapping, the CBVH further configured to allow input beams to pass in a second direction orthogonal to the first direction unaffected. The system further comprises a first lens configured to receive the diffracted beams and perform a Fourier transform on the input beams in the first direction, a second lens configured to receive the diffracted beams and focus the beams in the second direction to generate output beams, and a charged coupled device (CCD) configured to receive the outputs beams, the output beams used to provide spectral analysis of the input beams.

Another embodiment includes a method for performing spectral mapping and coded spectroscopy comprising receiving input beams at a cylindrical beam volume hologram (CBVH) to generate diffracted beams in a first direction and allowing beams to pass in a second direction unaffected, performing a spectral-spatial mapping of the input beams in the first direction, focusing the input beams in the second direction to generate an output, and receiving the output at a charged coupled device (CCD), the output providing a spectrum of the input beams.

Another embodiment includes an apparatus for performing spectral mapping and coded spectroscopy comprising means for receiving input beams at a cylindrical beam volume hologram (CBVH) to generate diffracted beams in a first direction and allowing beams to pass in a second direction unaffected, means for performing a spectral-spatial mapping of the input beams in the first direction for a range of wavelengths, means for focusing the input beams in the second direction to generate an output, and means for receiving the output at a charged coupled device (CCD), the output providing a spectrum of the input beams.

Yet another embodiment includes a method for performing spectral mapping and coded spectroscopy comprising receiving input beams at a cylindrical beam volume hologram (CBVH) to generate diffracted beams and to provide spectral-spatial mapping of the input beams in a first direction and different mappings in a second direction, obtaining a Fourier transform of the diffracted beams in the first direction, imaging the input beams in the second direction, and receiving the output at a charged coupled device (CCD), the output providing a spectrum of the input beams.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 5A-5B illustrate various outputs detected by a charge coupled device in the exemplary spectrometer from FIG. 3 where a lens with higher focusing power compared to the one used in FIGS. 4A-4D is utilized.

DETAILED DESCRIPTION

Figure 1:
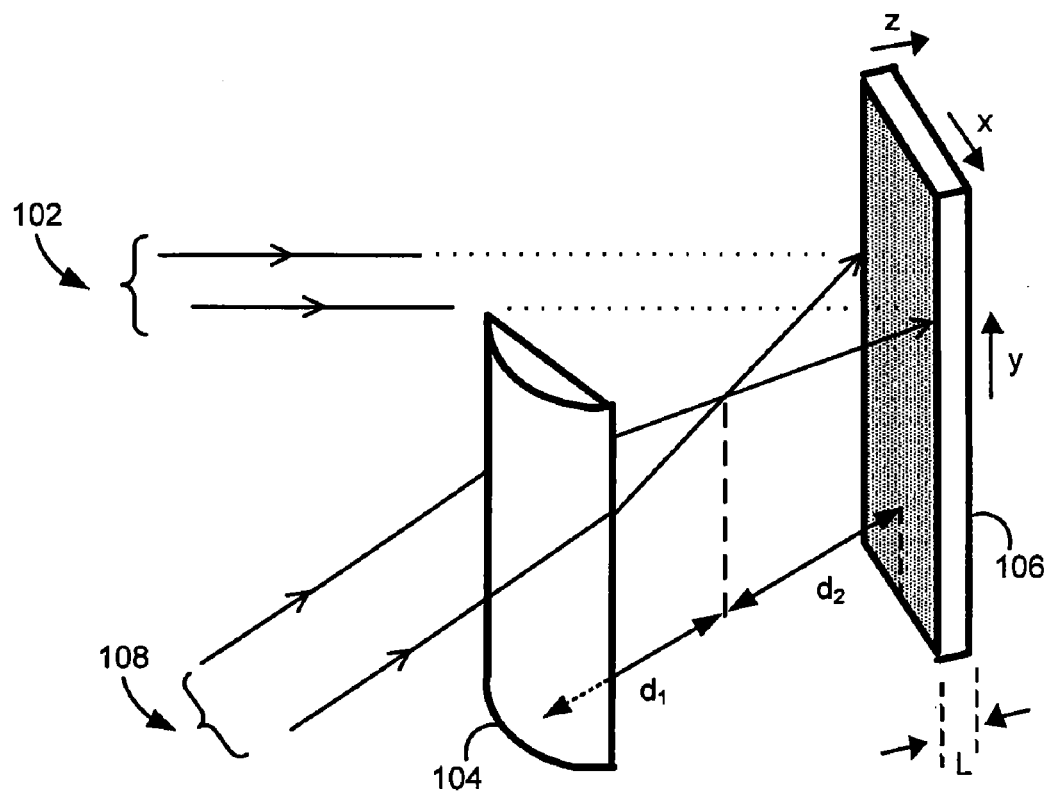
FIG. 1 is a diagram of an exemplary setup for recording a cylindrical beam volume hologram.

Embodiments described herein include systems and methods for expanding the spectral-spatial mapping into one or two dimensions and for performing coded spectroscopy. Embodiments of cylindrical beam volume holograms (CBVHs) provide spectral diversity in one direction without affecting the beam in the other direction. In addition, various embodiments of a spectrometer system utilizing a CBVH can be realized due to the independent treatment of the input beam in different directions. As a non-limiting example, in the direction parallel to the axis of the cylindrical beam in the recording configuration, different segments of the hologram can be recorded with different recording conditions (e.g., different plane waves) in order to provide two-dimensional spectral-spatial mapping at the output. This results in an increase in the range of the operating wavelength and/or the resolution of the system. Thus, embodiments of CBVHs provide for spatial mapping in two dimensions rather than in just one dimension, as provided by most conventional approaches to spectroscopy. Furthermore, it should be emphasized that the CBVH replaces the functionality of the input slit, the input collimating element, and the grating found in conventional spectrometers. Thus, embodiments of CBVHs provide spectrometers that have a fewer number of elements, thereby resulting in more compact, relatively low cost, robust spectrometers. Other embodiments of the spectrometer system described herein incorporate angular multiplexing where multiple holograms are multiplexed into each segment of the CBVH and different segments are spatially multiplexed into the CBVH in order to provide a coded mapping of the input spectrum onto a two-dimensional output. Simple post processing may then be performed in order to derive the spectrum of the input beam from the coded output with a high degree of accuracy.

Generally, to determine the spectral characteristics of an arbitrary beam, a mapping is performed of the scalar quantity of the spectrum (i.e., light intensity vs. different wavelengths) associated with the beam onto different spatial locations in an output plane. Typically, the spectrum of the input beam is spatially mapped onto a line in the output plane. This mapping can be efficiently implemented by modifying the beam only in one direction while the beam remains intact in the other direction.

As briefly described above, a key component in spectrometers is the wavelength sensitive (or dispersive) component that provides separation of different wavelength channels for detection purposes. Thin holograms (or gratings) are well-known candidates for achieving this because of their wavelength selectivity, which results in non-uniform diffraction of different wavelength channels of a collimated optical beam. Most of the optical spectrometers built based on this phenomenon exploit surface relief or thin film gratings, which primarily have single grating vectors. Exemplary embodiments of CBVHs described herein comprise thick volume holograms recorded using one or more plane waves and a cylindrical beam formed by a cylindrical lens. Because of the Bragg selectivity of the volume holograms, the separation of different wavelength channels is obtained for either a collimated beam or a diffuse beam. It should be appreciated that because of this unique property, the CBVH replaces various elements found in conventional spectrometers, including the input slit, the collimating lens or mirror, and the thin hologram or grating. In this respect, exemplary embodiments of the CBVH provide for compact and robust slitless spectrometers.

For embodiments of the spectrometer systems described herein, the spectral properties of the input beam are detected in a specific direction in the output plane while the orthogonal direction can be used to independently modify the beam through the system. It should be emphasized that embodiments of the spectrometer provide independent functionality in two orthogonal directions. As a result, unique applications can be realized by using embodiments of the CBVHs described herein. As a non-limiting example of one application, spectral-spatial mapping can be performed in two dimensions with a charged coupled device (CCD) placed at the output by recording different CBVHs into different segments of the hologram. Furthermore, multiple CBVHs may be multiplexed within each segment through angular multiplexing. As a result, coding can be performed on the mapping from the spectrum of the input beam into the various segments at the output.

In accordance with certain aspects of CBVHs described herein, FIG. 1 is a block diagram of an exemplary setup for recording a CBVH. Shown in FIG. 1 is a hologram (i.e., CBVH) 106 recorded using a plane wave 102 and a beam 108 focused by a cylindrical lens 104. For alternative embodiments, the hologram 106 may be recorded using two cylindrical beams formed by two cylindrical lenses. As illustrated in FIG. 1, the focus point of the cylindrical beam occurs at a distance $d_1$ behind the lens 104 and at a distance $d_2$ in front of the hologram 106. Furthermore, as depicted in FIG. 1, the hologram 106 has a thickness L. Depending on the application, the exemplary setup shown in FIG. 1 may be modified by adjusting the incident angles of the plane wave 102 and the cylindrical beam 108. It should be noted that beyond the cylindrical lens 104, the beam 108 is focused in the x-direction while it remains unmodified in the y-direction. The interference pattern between the cylindrical beam and the plane wave is recorded onto the hologram 106.

The properties of the CBVH can be explained from the plane wave expansion of the cylindrical beam. The electric field in the y-direction corresponding to a cylindrical beam 108 with the axis parallel to the y-axis, originated from a line source at $r_0=(0,y,-d)$ and monitored at $r=(x,y,z)$, is represented by a Hankel function of the zeroth order and of the first kind $H_0^{(1)}$. The field may be expressed by its Fourier transform as follows:

$$H_0^{(1)}(k|r - r_0|) = \frac{1}{\pi} \int \frac{1}{k_z} e^{jk_z(z+d)} e^{jk_x x} dk_x \quad (1)$$

In the equation above, $k_x$ and $k_z$ are the x- and z-components of the wave vector k. The amplitude of the wave vector k is the wave number $k=2\pi/\lambda$, where $\lambda$ is the wavelength. It should be noted that in the equation above, the $k_y$ component is 0 and therefore, the following holds true: $k_x^2+k_z^2=k^2$. Furthermore, it should be noted that the relation in the equation above is valid for all values of y. The hologram that is recorded by the cylindrical beam and a plane wave can be represented as the superposition of several simple gratings formed by the interference of each plane wave component of the cylindrical beam with the recording plane wave. Therefore, the diffraction from the CBVH can be found by superposing the diffracted components from the simple gratings. From Equation (1), it is clear that the cylindrical beam has no plane wave propagating in the y-direction. Therefore, no grating is formed in the y-direction and the recorded CBVH does not affect the reading beam in the y-direction.

Figure 2:
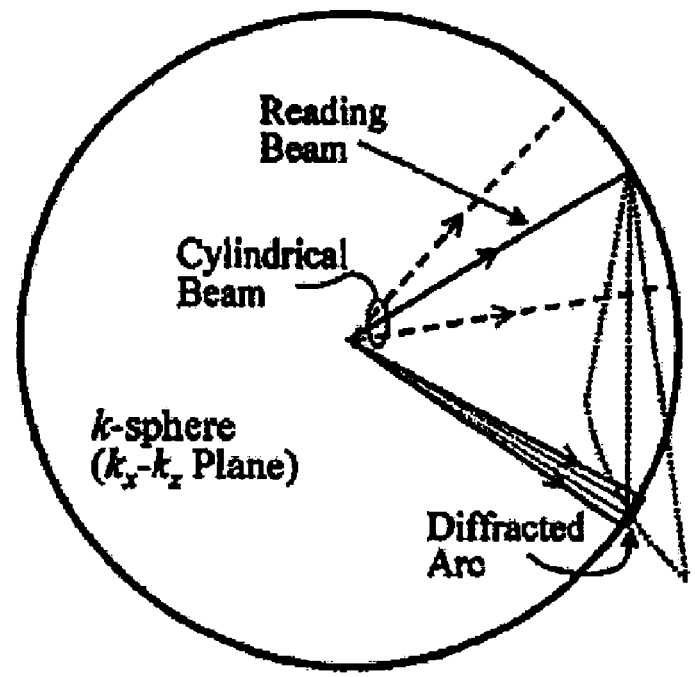
FIG. 2 depicts a k-sphere holographic representation of the cylindrical beam volume hologram from FIG. 1.

Reference is now made to FIG. 2, which depicts a k-sphere holographic representation of the CBVH from FIG. 1. The k-domain representation of the CBVH is depicted as a circle in the x-z plane and further illustrates some of the novel characteristics of the CBVH disclosed herein. The diverging beam coming from the cylindrical lens is represented by a sector. As neither the cylindrical beam nor the plane wave carry any propagation component in the y-direction, the two-dimensional k-domain representation shown in FIG. 2 is used for recording the CBVH. When the hologram is read by a plane wave mainly propagating in the direction of the cylindrical beam, a small set of k-vectors will be Bragg-matched to form the diffracted beam. If the angle of the reading beam is changed (within the angular extent of the recording cylindrical beam), another set of k-vectors will be Bragg-matched, but the direction of the diffracted beam will be unchanged. It should be noted that this is the main property of the CBVH which allows diffraction of a collimated or a diffuse input beam into a beam with very small spatial frequency (close to a plane wave). The CBVH exhibits this property even if the wavelength of the reading beam is different from the recording wavelength. In this respect, the spectrometer based on a CBVH does not require any collimating optics (i.e., an input slit and a collimating lens or mirror) to operate. It should be noted that the y-component of the reading beam will not be affected by the CBVH. Therefore, the hologram will only modify the properties of the beam in the x-direction. Furthermore, these properties are independent of those in the y-direction.

Figure 3:
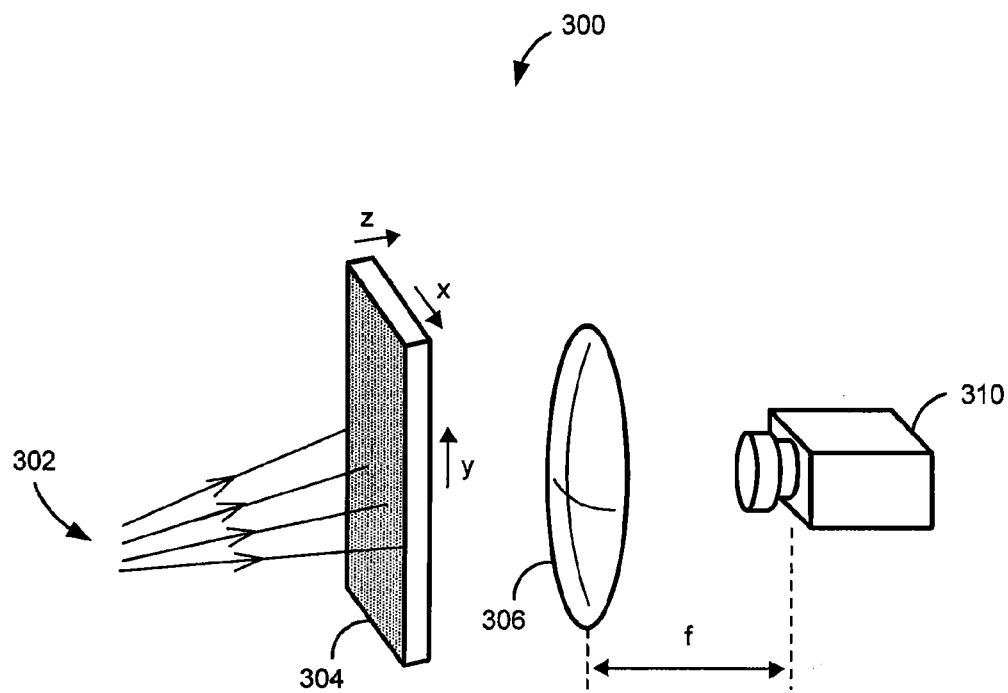
FIG. 3 is a diagram of an exemplary spectrometer incorporating the cylindrical beam volume hologram recorded from FIG. 1.

Reference is now made to FIG. 3, which is a diagram of an exemplary spectrometer incorporating the CBVH recorded from FIG. 1. In FIG. 3, the input beam 302 illuminates the hologram 304 primarily in the direction of the recording cylindrical beam. The diffracted beam from the hologram is then Fourier transformed using a lens 306 with a focal length f. For some embodiments, the lens 306 used in the spectrometer 300 may be either a spherical lens or a cylindrical lens, depending on the application. The output of the system is obtained using a CCD 310 located at the focal plane of the lens 306. In this regard, the spectrometer 300 may be utilized for two-dimensional spectral mapping. Furthermore, it should be emphasized that the CBVH 304 is not sensitive to the incident angles of the input beams (as explained above). This makes the use of CBVHs 304 suitable for diffuse light spectroscopy. As such, the spectrometer 300 is capable of dispersing diffuse light beams without the use of an input slit and a collimating lens or mirror.

Figures 4A, 4B:
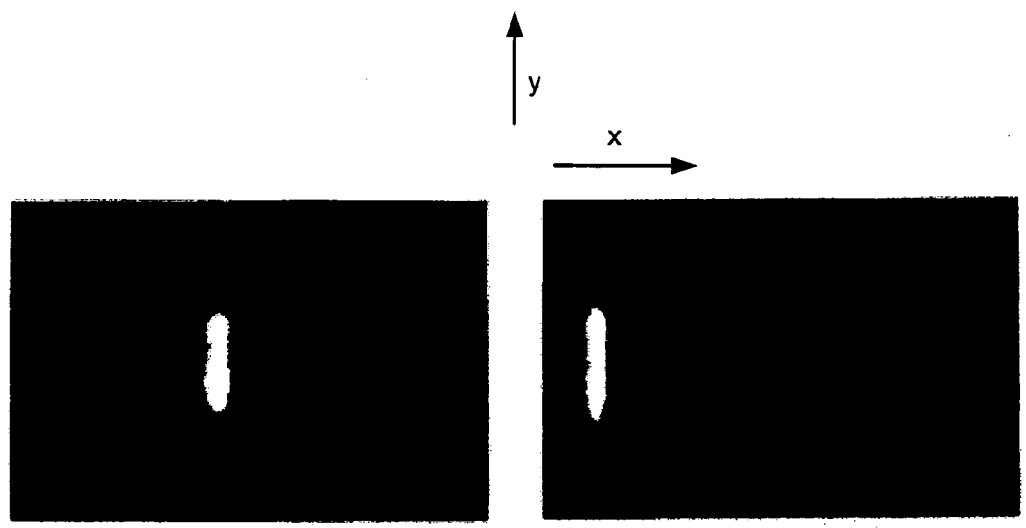
FIGS. 4A-4D illustrate various outputs detected by a charge coupled device in the exemplary spectrometer from FIG. 3.

FIGS. 4A-4D illustrate various outputs detected by a charge coupled device in the exemplary spectrometer from FIG. 3. To further illustrate some of the novel features of the CBVH, a white light is first passed through a monochromator. The output of the monochromator serves as the input into the spectrometer 300. As a non-limiting illustration, a spherical lens with a focal length of f=10 cm is utilized in the spectrometer setup of FIG. 3. Furthermore, the spherical lens is selected such that the ratio of the focal length for the lens to the lens diameter is F#=3.8. FIGS. 4A and 4B illustrate the outputs detected at the CCD 310 where the input beams have wavelengths $\lambda$=500 nm and $\lambda$=532 nm, respectively. It should be noted that while the spatial locations of the outputs vary in the x-direction as the wavelength changes, the outputs remain unchanged in the y-direction. The limited size in the y-direction is attributed to the limited divergence angle of the input beams in the y-direction.

Figures 4C, 4D:

To increase the divergence angle of the input beams in the y-direction, a rotating diffuser is inserted after the monochromator but in front of the CBVH 304. The addition of the rotating diffuser simulates an incoherent input beam. The outputs which correspond to the diffuse input beams at wavelengths $\lambda$=500 nm and $\lambda$=532 nm, respectively, are shown in FIGS. 4C and 4D. It should be noted that the spatial locations of the outputs in the x-direction remain the same as those in FIGS. 4A and 4B. However, the outputs span a greater distance in the y-direction. This is attributed to the wider range of incident angles in the input beam. Thus, as can be seen in FIGS. 4A-4D, a spectrometer 300 incorporating a CBVH 304 performs spectral separation in the x-direction for both diffuse and non-diffuse input beams while not affecting the beam in the y-direction. For the results shown in FIGS. 4A-4D, the input beam 302 undergoes a Fourier transformation in the y-direction because it is only affected by the spherical lens. It should be noted that if a cylindrical lens is used after the CBVH 304 rather than a spherical lens, the input beam 302 remains unchanged in the y-direction. That is, the input beam 302 is only affected in the x-direction and not the y-direction.

FIGS. 5A-5B illustrate various outputs detected by a charge coupled device in the exemplary spectrometer from FIG. 3 where a lens with higher focusing power compared to the one used in FIGS. 4A-4D is utilized. In another non-limiting illustration, the spherical lens has a smaller focal length-to-lens diameter ratio (F#=0.75) and smaller focal length (f=1.9 cm) is compared to the lens used for FIGS. 4A-4D. These parameters are chosen in order to provide a higher degree of focusing in the y-direction. The results are shown in FIGS. 5A and 5B for the incident wavelength of $\lambda$=532 nm.

FIG. 5A and reflect the output detected with no diffuser place in front of the CBVH such that a non-diffuse input beam enters the spectrometer. FIG. 5B shows the output detected with a rotating diffuser incorporated into the system (to generate a diffuse input beam). When compared to FIGS. 4A-4D, the distance in which the output spans in the y-direction is notably smaller in FIGS. 5A and 5B. Thus, the power distributed over a vertical strip in the y-direction is localized to a limited distance in the y-direction and the intensity to be detected is accordingly increased. It should be noted that the increase in the intensity achieved by focusing the input beam in the y-direction is ultimately limited by the Lagrange invariant of the system (or more generally by the constant radiance theorem). However, maximum intensity at the output can be achieved utilizing exemplary embodiments of the CBVH for even partially incoherent sources.

Figure 6:
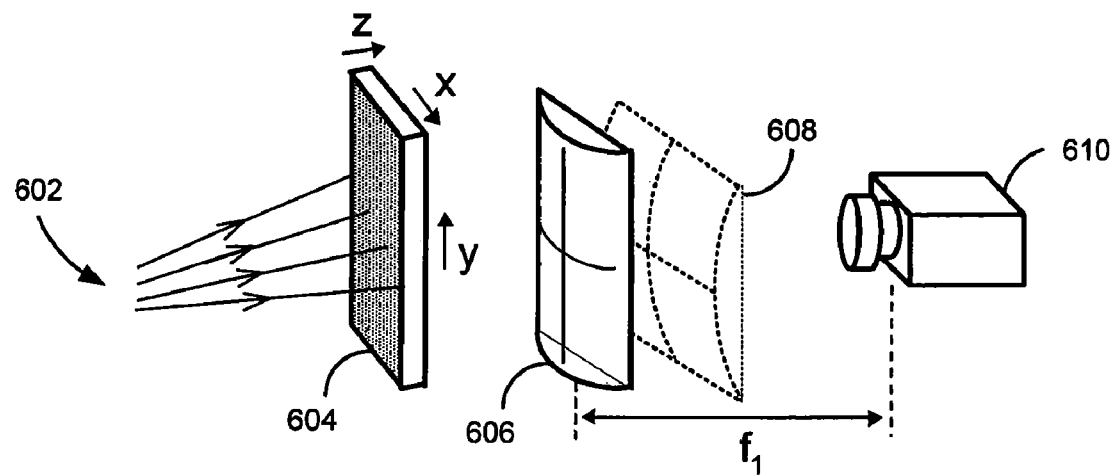
FIG. 6 is a diagram of an exemplary embodiment of a spectrometer incorporating the cylindrical beam volume hologram from FIG. 1 showing how one or two cylindrical lenses are utilized.

FIG. 6 is a diagram of an exemplary embodiment of a spectrometer incorporating the cylindrical beam volume hologram from FIG. 1 showing how one or two cylindrical lenses are utilized. It should be noted that for exemplary embodiments, a cylindrical lens 606 is used to perform a Fourier transform in the x-direction. Using another cylindrical lens 608 perpendicular to the cylindrical lens 606 used for performing the Fourier transform, the input beam 602 can be modified in the y-direction independently. This second lens 608 can be used to provide a higher degree of focusing in the y-direction. As discussed earlier, the input beam is unaffected by the hologram in the y-direction. Therefore, if the input beam is diverging in nature, the output at the CCD 610 will also be diverging in nature after the beam passes through the hologram and the first lens. Thus, the second cylindrical lens 608 is placed after the first cylindrical lens 606 such that the second lens 608 is orthogonal with respective to the first cylindrical lens 606 in order to focus the output in the y-direction.

In this case, the input beams can be mapped (or focused) to different spatial locations in the y-direction at the CCD 610. In this regard, the second cylindrical lens 608 focuses the output to specific locations at the CCD 610. In an alternative embodiment, the lens may be used to obtain the image of the hologram 604 at the CCD 610 in the y-direction. Since the diffracted beam propagates through different lenses 606, 608 in the x- and y-directions, respectively, the system provides spectral diversity in the x-direction while it maps the hologram 604 at the CCD 610 in the y-direction. It should be emphasized that this enables a degree of freedom in the design of the hologram in the y-direction. It should be noted that in alternative embodiments, the second cylindrical lens 608 can also be placed before the first cylindrical lens 606 to obtain similar results. It should be further noted that the functionality of the first cylindrical lens 606 can be further integrated into the volume hologram if the CBVH is recorded using two cylindrical beams. In this regard, for the recording arrangement shown in FIG. 1, the plane wave should be replaced by a converging cylindrical beam focused after the hologram. The interface of a diverging cylindrical beam with a converging cylindrical beam is recorded inside the hologram. Therefore, it should be appreciated that the spectrometer arrangement becomes even more compact for such embodiments. Furthermore, the functionalities of the first lens 606 and the second lens 608 can be integrated into the CBVH if the recording plane wave of the arrangement in FIG. 1 is replaced by a beam that is converging in both x- and y-directions. This results in further reduction of the number of elements and the size of the spectrometer.

Figure 7:
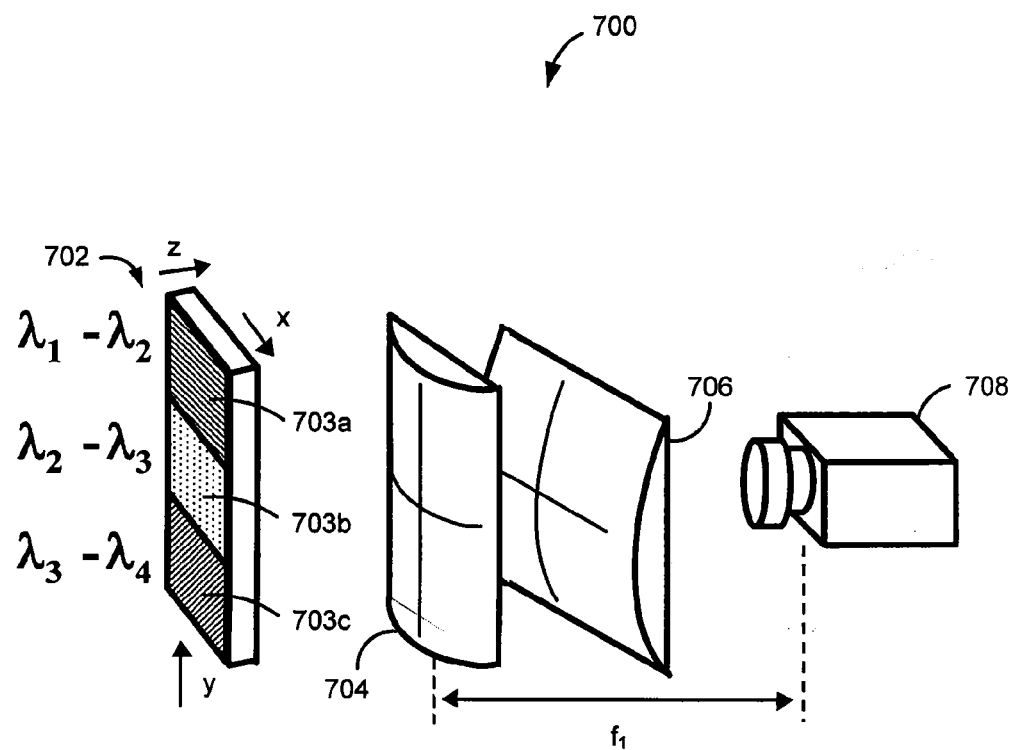
FIG. 7 is a diagram of an alternative embodiment of a spectrometer incorporating the cylindrical beam volume hologram from FIG. 1 where different wavelength ranges are diffracted from different locations of the hologram and mapped to different segments on the CCD in the y-direction.

For some embodiments, the hologram can be divided in the y-direction into several regions or segments. Within each region, a corresponding hologram may be recorded to map a certain range of wavelengths of the input beam to a specific location in the output. Reference is now made to FIG. 7, which is a diagram of an alternative embodiment of a spectrometer incorporating the cylindrical beam volume hologram from FIG. 1 where different wavelength ranges are diffracted from different locations of the hologram and mapped to different segments on the CCD in the y-direction. FIG. 7 shows an embodiment where three different segments 703a, 703b, 703c are recorded in the CBVH 702. In the arrangement shown, the top hologram 703a diffracts the input beam in the range of $\lambda_1$ to $\lambda_2$. The spectral range corresponding to the middle hologram 703b diffracts the input beam in the range of $\lambda_2$ to $\lambda_3$. Likewise, the bottom hologram 703c diffracts the input beam in the range of $\lambda_3$ to $\lambda_4$. Therefore, the one-dimensional spectral diversity is mapped onto two dimensions at the CCD 708. In this regard, embodiments of the hologram 702 described in FIG. 7 is spatially multiplexed to provide two-dimensional spectral-spatial mapping (i.e. spectral wrapping).

It should be appreciated that in this respect, the use of the design flexibility in the y-direction is not limited to the cases described here. The spectral wrapping technique may also be used in conjunction with thicker recording material in order to improve both resolution and spectral range. While there are some trade-off between the ultimate resolution and operating spectral range in every spectrometer, the optimal use of the spectral wrapping property of CBVH spectrometer minimizes this trade-off. It should be noted that the "segmented" or partitioned hologram 702 may be recorded in either a single step or in sequential steps, depending on the recording setup utilized. For example, a spatial light modulator or a mask may be incorporated into the setup. Also, since the holograms 702 are recorded onto different regions or segments 703a-c of the recording material, the full dynamic range of the material can be used for recording each hologram 702 to obtain high diffraction efficiency.

In other embodiments, the spectral wrapping can be obtained by angularly multiplexing a plurality of CBVHs in the y-direction. Different holograms can be multiplexed using the same cylindrical beam and several plane waves with different angles of propagation in the y-direction. The arrangement of the spectrometer for this embodiment is similar to the arrangement shown in FIG. 7. In other embodiments, both cylindrical lenses can be used to obtain the Fourier transform of the beam in both directions. In yet other embodiments, the combination of the two lenses can be implemented using a spherical lens.

Figure 8:
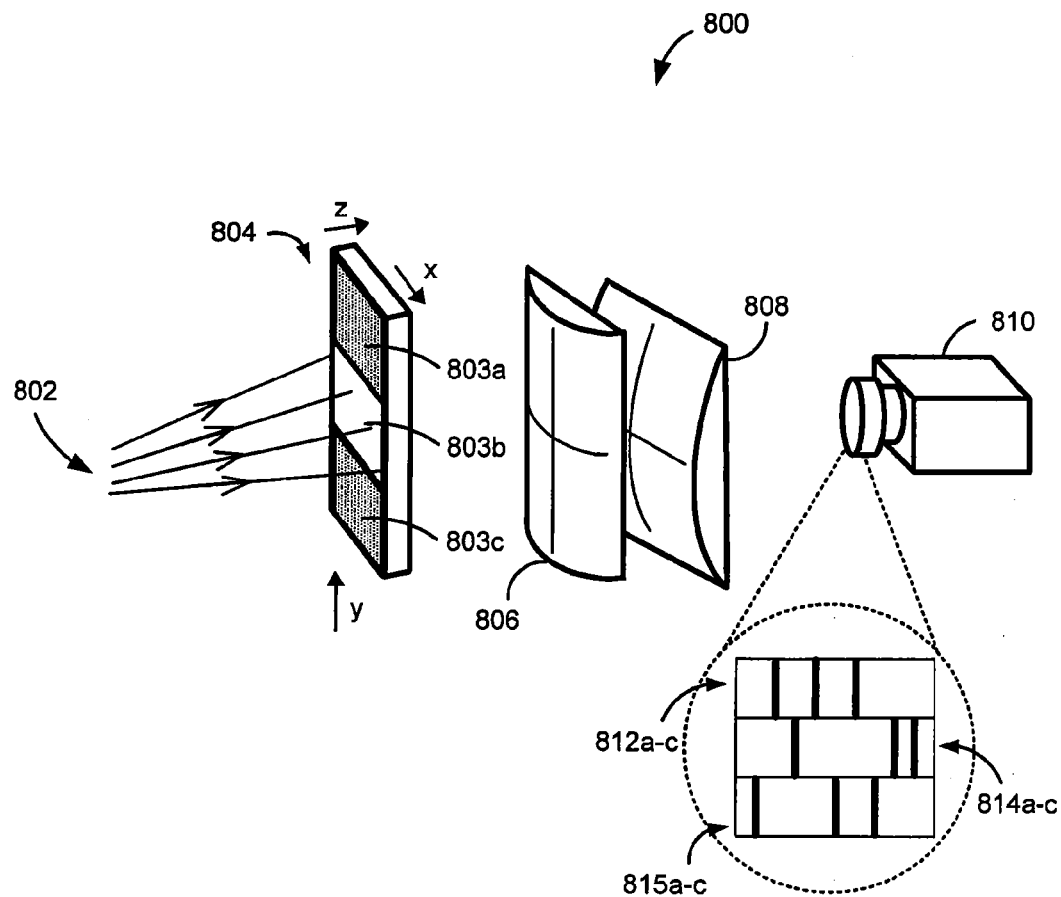
FIG. 8 is a diagram of an alternative embodiment of a spectrometer incorporating the cylindrical beam volume hologram from FIG. 1 where different segments of the hologram in the y-direction are angularly multiplexed to provide different spatial-spectral maps on different segments of the CCD in the y-direction.

In other embodiments, multiple holograms may be multiplexed to a particular segment. Reference is now made to FIG. 8, which is a diagram of an alternative embodiment of a spectrometer incorporating the cylindrical beam volume hologram from FIG. 1 where different segments of the hologram in the y-direction are utilized. In these segments, different holograms are angularly multiplexed in the x-direction to provide different spatial-spectral maps on different segments of the CCD in the y-direction. FIG. 8 shows the segmented CBVH 804 from FIG. 7 but where multiple holograms are angularly multiplexed in the x-direction into each segment 803a-c. The resulting spectral-spatial mappings which correspond to the segment 803a, 803b, and 803c are shown as different patterns 815a-c, 814a-c, 812a-c on the CCD 810, respectively, for reading with a monochromatic beam. Therefore, each wavelength is mapped to more than one location in each segment since it is diffracted from an angularly multiplexed hologram. The maps for different wavelength may overlap in each segment, but the difference in the mappings of different segments provide enough information to obtain the correct contribution of each wavelength in the spectrum of the input beam.

To incorporate angular multiplexing, multiple holograms are recorded by varying the incident angle of the plane waves. Thus, each angle-multiplexed CBVH may be recorded using a fixed cylindrical beam and a plane wave with a different (adjustable) incident angle with respect to the other holograms. As a non-limiting example, three different incident angles would be used to record three different holograms. Further details regarding angular multiplexing can be found in U.S. patent application Ser. No. 11/459,102 (Pub. No. 2007/0030490), filed Jul. 21, 2006, herein incorporated by reference in its entirety.

In the non-limiting example shown in FIG. 8, three different holograms are multiplexed into a single segment 803a. Using one segment 803a-c of the hologram, the total power in the output corresponding to a monochromic input may be increased by a factor of approximately 3 times when compared to the case where a single CBVH is used, since three diffraction components will be collected at the CCD 810. Each wavelength component is mapped to three vertical strips 812a-c, 814a-c, 815a-c, as shown in FIG. 8. However, it should be noted that the resolution is reduced since a larger region is assigned to one input wavelength. If the segments 803a-c of the hologram 804 are designed differently to provide independent mapping conditions in different segments for each input wavelength component, post processing may be used to compensate for the reduction in the resolution. In each segment 803a-c, the output signal 812a-c, 814a-c, 815a-c corresponding to different wavelength components overlap in the output plane, but the independent mapping obtained using multi-segmented hologram 804 provides enough information to solve for (or estimate) the correct spectral contents of the input beam. In this regard, coded spectroscopy is achieved using angular multiplexing in each segment and spatial multiplexing of different segments, and results in an increase in the power detected for a given wavelength without sacrificing the resolution.

Figure 9:
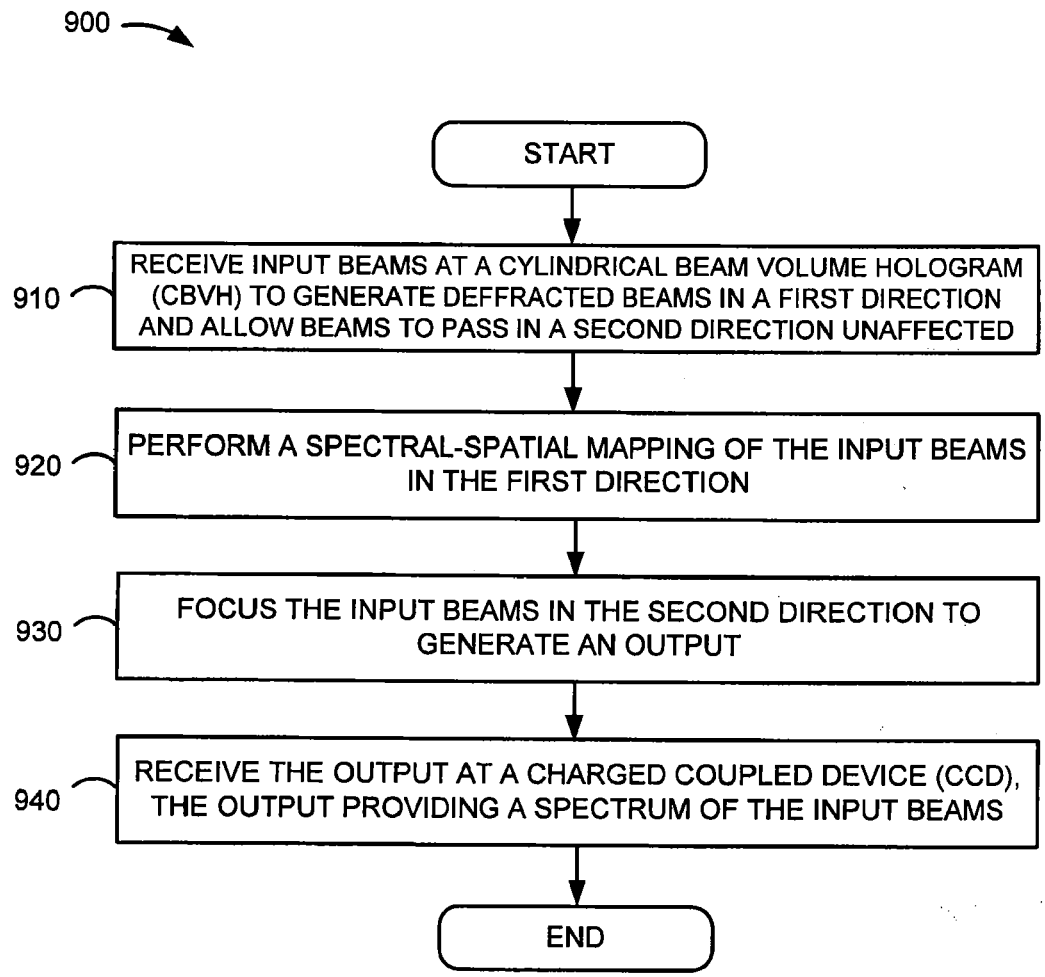
FIG. 9 is a flowchart for an embodiment of a method for performing spectral analysis using the spectrometer in FIG. 6.

Reference is made to FIG. 9, which is a flowchart for an embodiment of a method for performing spectral analysis using the spectrometer in FIG. 6. Beginning in step 910, input beams are received at a cylindrical beam volume hologram (CBVH) where diffracted beams are generated in a first direction and the beam is allowed to pass through unaffected in a second (orthogonal) direction. In step 920, a spectral-spatial mapping is performed on the input beams in a first direction. In step 930, the input beams are focused in the second direction to generate an output. In step 940, the output is received at a charged coupled device (CCD) where the output provides a spectrum of the input beams.

Figure 10:
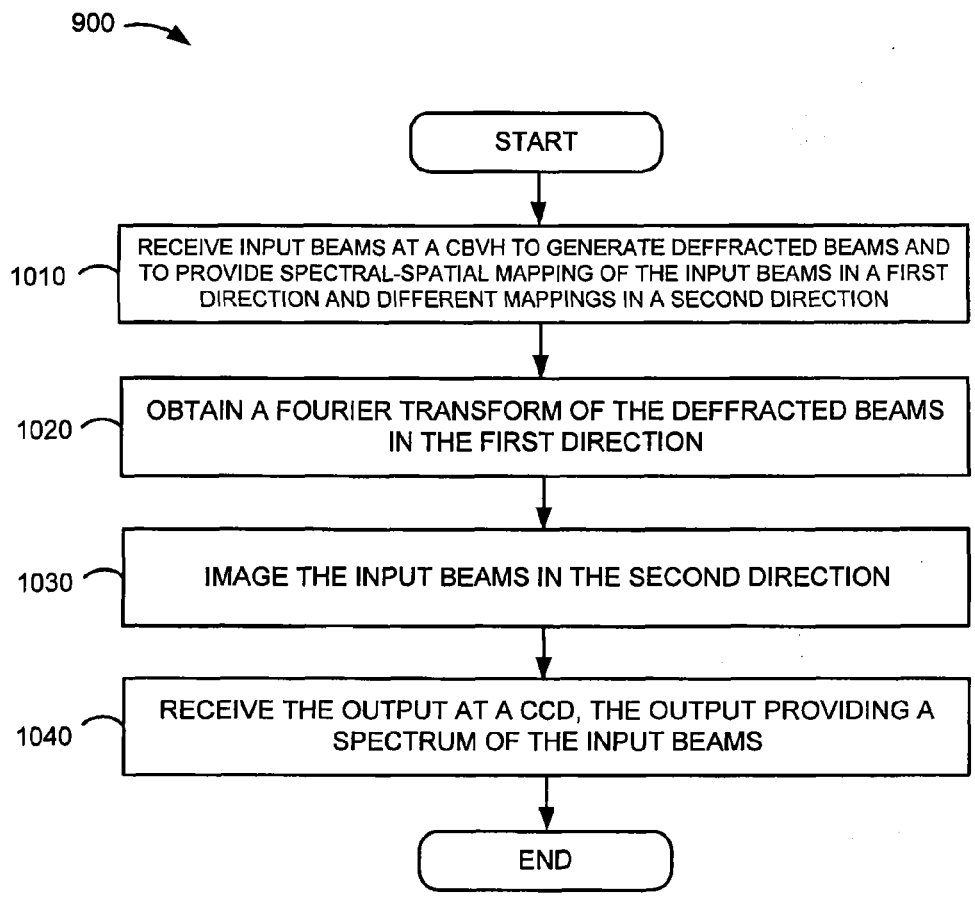
FIG. 10 is a flowchart for an alternative embodiment of a method for performing spectral analysis using the spectrometer in FIG. 6.

Reference is made to FIG. 10, which is a flowchart for an alternative embodiment of a method for performing spectral analysis using the spectrometer in FIG. 6. Beginning in step 1010, input beams are received at a cylindrical beam volume hologram (CBVH) to generate diffracted beams and to provide spectral-spatial mapping of the input beams in a first direction and different mappings in a second direction. In step 1020, a Fourier transform is obtained for the diffracted beams in the first direction. Next, in step 1030, the input beams are imaged (or focused) in the second direction. In step 1040 the output is received at a charged coupled device (CCD), the output providing (with possible post-processing) a spectrum of the input beams.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A spectrometer for performing spectral-spatial mapping and coded spectroscopy comprising:
   a cylindrical beam volume hologram (CBVH), the CBVH configured to receive input beams and generate diffracted beams in a first direction to perform spectral-spatial mapping, the CBVH further configured to allow input beams to pass in a second direction orthogonal to the first direction unaffected;
   a first lens configured to receive the diffracted beams and perform a Fourier transform on the input beams in the first direction;
   a second lens configured to receive the diffracted beams and focus the beams in the second direction to generate output beams; and
   a charged coupled device (CCD) configured to receive the outputs beams, the output beams used to provide spectral analysis of the input beams.

2. The spectrometer of claim 1, wherein the CBVH is partitioned into a plurality of segments spanning the second direction.

3. The spectrometer of claim 2, wherein each of the plurality of segments within the CBVH is configured to provide a spectral-spatial mapping of a range of wavelengths, the plurality of segments providing a two-dimensional spectral wrapping.

4. The spectrometer of claim 2, wherein a plurality of CBVHs are multiplexed into each of the plurality of segments to provide coded spectral-spatial mapping.

5. The spectrometer of claim 4, wherein multiplexing the plurality of CBVHs is performed using angular multiplexing.

6. The spectrometer of claim 1, wherein the CBVHs are angularly multiplexed in the second direction.

7. The spectrometer of claim 6, wherein each of the plurality of angularly multiplexed CBVHs is configured to provide a spectral-spatial mapping of a range of wavelengths, the plurality of CBVHs providing a two-dimensional spectral wrapping.

8. The spectrometer of claim 1, wherein the CBVH is recorded using a plane wave and a beam focused by a cylindrical lens.

9. The spectrometer of claim 1, wherein the CBVH is recorded using two cylindrical beams formed by two cylindrical lenses.

10. The spectrometer of claim 1, wherein the CBVH is recorded using a cylindrical beam and a beam that converges in both the first direction and the second direction.

11. The spectrometer of claim 1, wherein the first and second lens is one of a cylindrical lens and a spherical lens.

12. The spectrometer of claim 8, wherein a different incident angle of the plane wave, in either the first direction or the second direction, is used to record each of the plurality of holograms.

13. The spectrometer of claim 4, further comprising a post-processing module configured to derive a spectrum of the input beams by post-processing the output received at the CCD.

14. A method for performing spectral mapping and coded spectroscopy comprising:
   receiving input beams at a cylindrical beam volume hologram (CBVH) to generate diffracted beams in a first direction and allowing beams to pass in a second direction unaffected;
   performing a spectral-spatial mapping of the input beams in the first direction;
   focusing the input beams in the second direction to generate an output; and
   receiving the output at a charged coupled device (CCD), the output providing a spectrum of the input beams.

15. The method of claim 14, further comprising partitioning the CBVH into a plurality of segments, the segments spanning the second direction.

16. The method of claim 15, wherein each of the plurality of segments within the CBVH is configured to provide a spectral mapping of a range of wavelengths, wherein each of the plurality of segments maps a wavelength range into a separate region at the output.

17. The method of claim 15, further comprising multiplexing a plurality of holograms into each segment.

18. The method of claim 17, wherein multiplexing the plurality of holograms is performed using angular multiplexing.

19. The method of claim 14, wherein the CBVH is recorded using a plane wave and a beam focused by a cylindrical lens.

20. The method of claim 14, wherein the CBVH is recorded two cylindrical beams formed by two cylindrical lenses.

21. The method of claim 14, wherein the CBVH is recorded using a cylindrical beam and a beam that focuses in both the first direction and the second direction.

22. The method of claim 14, wherein the first and second lens is one of a cylindrical lens and a spherical lens.

23. The method of claim 19, wherein a different incident angle of the plane wave, in either the first direction or the second direction, is used to record each of the plurality of holograms.

24. The method of claim 17, further comprising post-processing the output beams received at the CCD to derive a spectrum of the input beams.

25. The method of claim 14, wherein focusing the input beams in the second direction comprises increasing an intensity and decreasing a spatial extent of the input beams.

26. An apparatus for performing spectral mapping and coded spectroscopy comprising:
   means for receiving input beams at a cylindrical beam volume hologram (CBVH) to generate diffracted beams in a first direction and allowing beams to pass in a second direction unaffected;
   means for performing a spectral-spatial mapping of the input beams in the first direction for a range of wavelengths;
   means for focusing the input beams in the second direction to generate an output; and
   means for receiving the output at a charged coupled device (CCD), the output providing a spectrum of the input beams.

27. The apparatus of claim 26, further comprising means for partitioning the CBVH into a plurality of segments, the segments spanning the second direction.

28. The apparatus of claim 27, wherein each segment within the CBVH is configured to provide a spectral mapping of a range of wavelengths.

29. The apparatus of claim 27, further comprising means for multiplexing a plurality of holograms into each segment.

30. A method for performing spectral mapping and coded spectroscopy comprising:
   receiving input beams at a cylindrical beam volume hologram (CBVH) to generate diffracted beams and to provide spectral-spatial mapping of the input beams in a first direction and different mappings in a second direction;
   obtaining a Fourier transform of the diffracted beams in the first direction;
   imaging the input beams in the second direction; and
   receiving the output at a charged coupled device (CCD), the output providing a spectrum of the input beams.

31. The method of claim 30, further comprising partitioning the CBVH into a plurality of segments, the segments spanning the second direction.

32. The method of claim 31, wherein each segment within the CBVH is configured to provide a spectral mapping of a range of wavelengths.

33. The method of claim 31, further comprising multiplexing a plurality of holograms into each segment.

34. The method of claim 30, wherein different segments provide different coded mappings of the input spectrum onto different segments of the CCD.

* * * * *

UNITED STATES PATENT AND TRADEMARK OFFICE
CERTIFICATE OF CORRECTION

PATENT NO. : 8,213,008 B2  
APPLICATION NO. : 12/671166  
DATED : July 3, 2012  
INVENTOR(S) : Omid Momtahan, Chao Ray Hsieh and Ali Adibi Page 1 of 1

It is certified that error appears in the above-identified patent and that said Letters Patent is hereby corrected as shown below:

At column 10, line 11, delete "the CBVHs" and replace with --a plurality of CBVHs--.

At column 10, line 31, delete "the plurality" and replace with --a plurality--.

At column 10, line 32, delete "holograms" and replace with --CBVHs--.

At column 11, line 8, delete "the plurality" and replace with --a plurality--.

At column 11, line 9, delete "holograms" and replace with --CBVHs--.

Signed and Sealed this  
Ninth Day of April, 2013

Teresa Stanek Rea  
*Acting Director of the United States Patent and Trademark Office*